(12) United States Patent
Lee et al.

(10) Patent No.: US 11,291,374 B2
(45) Date of Patent: Apr. 5, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: So Young Lee, Daejeon (KR); Ka Ram Choi, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 99 days.

(21) Appl. No.: 16/707,883

(22) Filed: Dec. 9, 2019

(65) Prior Publication Data

US 2020/0323437 A1 Oct. 15, 2020

(30) Foreign Application Priority Data

Apr. 10, 2019 (KR) .................. 10-2019-0041753

(51) Int. Cl.
*A61B 5/0205* (2006.01)
*A61B 5/00* (2006.01)
*A61B 5/1455* (2006.01)
*A61B 5/01* (2006.01)
*A61B 5/145* (2006.01)
(Continued)

(52) U.S. Cl.
CPC .......... *A61B 5/02055* (2013.01); *A61B 5/01* (2013.01); *A61B 5/14532* (2013.01); *A61B 5/14546* (2013.01); *A61B 5/14551* (2013.01); *A61B 5/20* (2013.01); *A61B 5/318* (2021.01); *A61B 5/4866* (2013.01); *A61B 5/4875* (2013.01); *A61B 5/7264* (2013.01); *A61B 5/7275* (2013.01);
(Continued)

(58) Field of Classification Search
CPC ... A61B 5/02055; A61B 5/318; A61B 5/4866; A61B 5/14551; A61B 5/01; A61B 5/7275; A61B 5/7264; A61B 5/14546; A61B 5/4875; A61B 5/20; A61B 5/14532; A61B 5/0245; A61B 5/02108; A61B 5/0059; A61B 5/024
See application file for complete search history.

(56) References Cited

U.S. PATENT DOCUMENTS 9,554,738 B1 * 1/2017 Gulati .................. A61B 5/0075
10,278,591 B2 5/2019 Gil
(Continued)

FOREIGN PATENT DOCUMENTS

JP 10-328170 A 12/1998
JP WO2016/117520 A1 7/2016
(Continued)

*Primary Examiner* — Brian T Gedeon
*Assistant Examiner* — Joshua Andrew Schum-Houck
(74) *Attorney, Agent, or Firm* — Sughrue Mion, PLLC

(57) ABSTRACT

Provided is an apparatus for estimating bio-information which estimates bio-information from a user. The apparatus for estimating bio-information according to an embodiment of the present disclosure includes: a spectrometer configured to obtain, absorbance from a user; a physiological information obtainer configured to obtain metabolic and physiological information including a concentration of carbon dioxide ($CO_2$); and a processor configured to estimate bio-information based on the absorbance and the metabolic, and physiological information by using a predictive model corresponding to the obtained metabolic and physiological information.

19 Claims, 8 Drawing Sheets

(51) Int. Cl.
  *A61B 5/021*   (2006.01)
  *A61B 5/20*    (2006.01)
  *A61B 5/318*   (2021.01)
  *A61B 5/0245*  (2006.01)

(52) U.S. Cl.
  CPC ......... *A61B 5/0245* (2013.01); *A61B 5/02108* (2013.01)

(56) References Cited

U.S. PATENT DOCUMENTS

| | | |
|---|---|---|
| 2008/0269580 A1 | 10/2008 | Balistrer et al. |
| 2009/0299154 A1* | 12/2009 | Segman ................ A61B 5/445 600/301 |
| 2010/0105996 A1 | 4/2010 | Segman |
| 2011/0184683 A1* | 7/2011 | Soller ................ G01N 21/3577 702/85 |
| 2012/0271133 A1 | 10/2012 | Gal et al. |
| 2015/0119661 A1* | 4/2015 | Gilbert ............... A61B 5/14539 600/316 |
| 2015/0369725 A1* | 12/2015 | Carvalho Sousa ......................... A61B 5/14532 435/288.7 |
| 2016/0157733 A1* | 6/2016 | Gil ..................... A61B 5/14551 600/301 |
| 2016/0338623 A1 | 11/2016 | Tholl et al. |
| 2018/0000386 A1 | 1/2018 | Yamakawa |
| 2018/0035933 A1* | 2/2018 | Ho ...................... A61B 5/7203 |
| 2018/0228409 A1 | 8/2018 | Kim |
| 2018/0228433 A1 | 8/2018 | Kim |
| 2020/0129095 A1 | 4/2020 | Lee et al. |

FOREIGN PATENT DOCUMENTS

| | | |
|---|---|---|
| KR | 10-1512076 B1 | 4/2015 |
| KR | 10-2015-0095346 A | 8/2015 |
| KR | 10-2020-0047981 A | 5/2020 |
| WO | 2017129634 A1 | 8/2017 |

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2019-0041753, filed on Apr. 10, 2019, in the Korean Intellectual Property Office, the disclosure of which is incorporated herein by reference in its entirety.

BACKGROUND

1. Field

Apparatuses and methods consistent with example embodiments relate to estimating bio-information based on spectral absorbance and metabolic and physiological indicators.

2. Description of the Related Art

Diabetes is a chronic disease that causes various complications and can be hardly cured, such that people with diabetes are advised to check their blood glucose regularly to prevent complications. In particular, when insulin is administered to control blood glucose, the blood glucose levels have to be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease infections due to the use of injection. Recently, research has been conducted on methods of non-invasively estimating bio-information, such as blood glucose, by performing spectrum analysis using a spectrometer without blood sampling.

SUMMARY

According to an aspect of an embodiment, there is provided an apparatus for estimating bio-information, the apparatus including: a spectrometer configured to obtain a light absorbance spectrum from a user: one or more sensors configured to obtain metabolic and physiological information of the use, the obtained metabolic and physiological information including a carbon dioxide ($CO_2$) concentration of tire user; and a processor configured to identify a predictive model corresponding to a type of the obtained metabolic and physiological information, among a plurality of predictive models trained based on different combinations of a reference light absorbance spectrum and a plurality of metabolic and physiological information types, and estimate bio-information based on the absorbance and the metabolic and physiological information by using the identified predictive model.

The spectrometer may include: a light source configured to emit a light onto the user; and a detector configured to detect the light scattered or reflected from the user.

The one or more sensors may include at least one of an optical gas sensor configured to obtain the $CO_2$ concentration of the user, and a pulse wave sensor configured to obtain a pulse wave reflected from the user.

The metabolic and physiological information may further include at least one of a body temperature, a heart rate (HR), a heart rate variability (HRV), and a pulse wave feature.

The one or more sensors may further include: a body temperature sensor configured to measure the body temperature; and an electrocardiogram sensor configured to obtain at least one of the HR and the HRV.

The one or more sensors may be further configured to estimate the body temperature information based on the obtained light absorbance spectrum.

The one or more sensors may include a pulse wave sensor configured to obtain a pulse wave signal, wherein the processor may be further configured to obtain at least one of the HR, the HRV, and the pulse wave feature based on the pulse wave signal.

Upon receiving a request for estimating bio-information, the processor may check an operating state of the spectrometer and each sensor of the physiological information obtainer, and select a predictive model for use in estimating bio-information from among the plurality of predictive models based on the checking result.

Upon receiving a request for estimating bio-information, the processor may check an operating state of the spectrometer and each sensor of the physiological information obtainer, and controls operation of the spectrometer or the each sensor or provides guidance on the operation for a user based on the predictive model for use in estimating bio-information.

The predictive model may be generated by using one of linear regression analysis, non-linear regression analysis, Partial Least Squares (PLS), Bayesian Network, Hidden Markov Model, Decision Tree, Random Forest, Support Vector Machine, Convolutional Neural Network, and Deep Neural Network.

The bio-information may include one or more of blood glucose, cholesterol, triglyceride, body water, lactate, protein, and uric acid.

The apparatus may further include an output interface configured to output at least one of the obtained absorbance, the obtained metabolic and physiological information, and a processing result of the processor.

According to an aspect of another example embodiment, there is provided a method of estimating bio-information, including: obtaining a light absorbance spectrum from a user; obtaining metabolic and physiological information of the user, the metabolic and physiological information including a concentration of carbon dioxide ($CO_2$) of the user; identifying a predictive model corresponding to as type of the obtained metabolic and physiological information, among a plurality of predictive models trained based on different combinations of a reference light absorbance spectrum and a plurality of metabolic and physiological information types, and estimating bio-information based on the obtained light absorbance spectrum and the obtained metabolic and physiological information by using the identified predictive model.

The metabolic and physiological information may further include at least one of a body temperature, a heart rate (HR), a heart rate variability (HRV), and a pulse wave feature.

The obtaining the light absorbance spectrum may be performed by a spectrometer, and the obtaining metabolic and physiological information may be performed by one or more sensors. The estimating the bio-information may include, upon receiving a request for estimating bio-information, checking an operating state of the spectrometer and each of the one or more sensors, and selecting the predictive model based on a result of checking the operating state of the spectrometer and each of the one or more sensors.

The obtaining the light absorbance spectrum may be performed by a spectrometer, and the obtaining metabolic and physiological information may be performed by one or more sensors. The estimating the bio-information may include, upon receiving a request for estimating bra-information, checking an operating state of the spectrometer and each of the one or more sensors, and controlling an operation of the spectrometer or each of the one or more sensors, and providing the user with guidance on the operation based on the identified predictive model.

The method may further include outputting at least one of the obtained light absorbance spectrum, the obtained metabolic and physiological information, and the estimated bio-information.

The different combinations of the reference built absorbance spectrum and the plurality of metabolic and physiological information types may include a combination of the reference light absorbance spectrum and a reference carbon dioxide concentration.

The different combinations of the reference light absorbance spectrum and the plurality of metabolic and physiological information types may include at least one of a first combination of the reference light absorbance spectrum and a reference carbon dioxide concentration; a second combination of the reference light absorbance spectrum, the reference carbon dioxide concentration, and a reference body temperature; a third combination of the reference light absorbance spectrum, the reference carbon dioxide concentration, the reference body temperature, and a reference heart rate; a fourth combination of the reference light absorbance spectrum, the reference carbon dioxide concentration, the reference body temperature, the reference heart rate, and a reference heart rate variability; and a fifth combination of the reference light absorbance spectrum, the reference carbon dioxide concentration, the reference body temperature, the reference heart rate, the reference heart rate variability, and a reference pulse wave feature.

The identifying the predictive model may include identifying the predictive model which is trained based one of the first to the fifth combinations, as the predictive model for estimating the bio-information.

BRIEF DESCRIPTION OF THE DRAWINGS

The above and/or other aspects will be more apparent by describing certain example embodiments, with reference to the accompanying drawings, in which.

Figure 1A:
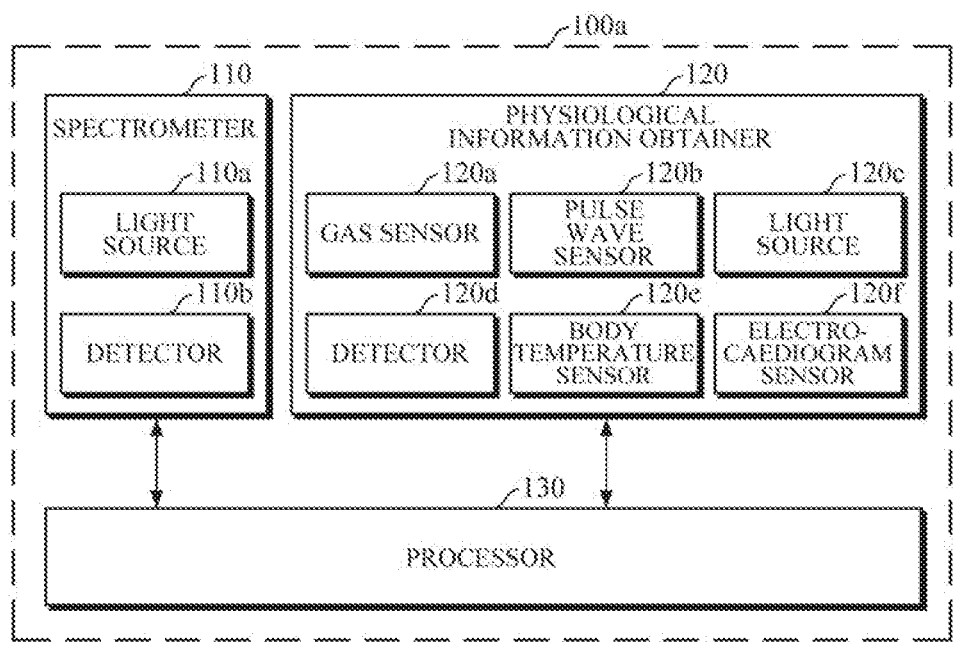
FIG. 1A is a block diagram illustrating an apparatus for estimating bio-information according to an embodiment of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, of a combination thereof.

Expressions such as "at least one of," when preceding a list of elements, modify the entire list of elements and do not modify the individual elements of the list. For example, the expression, "at least one of at, b, and c," should be understood as including only a, only b, only c, both a and b, both a and c, both b and c, all of a, b, and c, or any variations of the aforementioned examples.

Figure 1B:
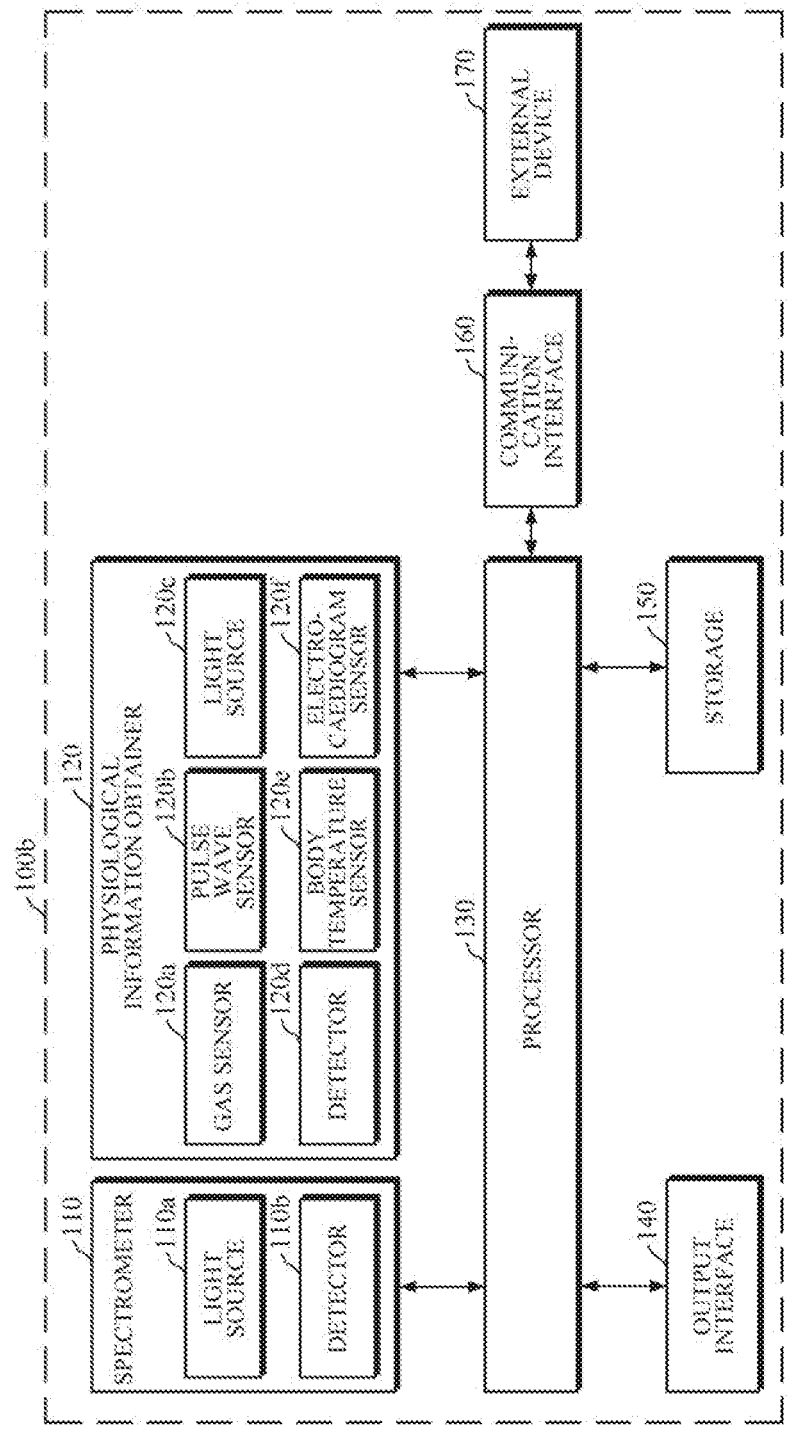
FIG. 1B is a block diagram, illustrating an apparatus for estimating bio-information according to another embodiment of the present disclosure.
Figure 2:
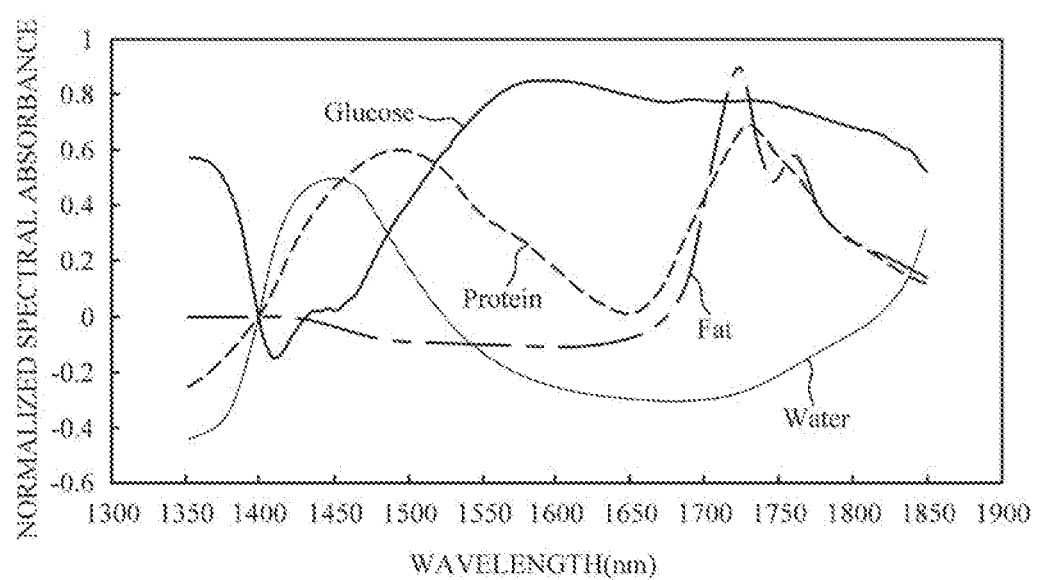
FIG. 2 is a graph illustrating optical wavelength versus absorbance of in vivo components.

FIGS. 1A and 1B are block diagrams illustrating an apparatus for estimating bio-information according to embodiments of the present disclosure. FIG. 2 is a graph illustrating optical wavelength versus absorbance of in vivo components.

The bio-information estimating apparatuses 100a and 100b are apparatuses for estimating bio-information, such as blood glucose, cholesterol, trialyceride, body water, lactate, protein, uric acid, and the like, and may be embedded in an electronic device such as a smartphone, a tablet PC, a desktop computer, a laptop computer, and the like, or in a medical device used in a specialized medical institution. Alternatively, the bio-information estimating apparatuses 100a and 100b may be manufactured as an independent device, such as a wristwatch-type wearable device, a bracelet-type wearable device, a wristband-type wearable device, a ring-type wearable device, a glasses-type wearable device, a headband-type wearable device and the like, which may be worn on an object.

Referring to FIGS. 1A and 1B, the bio-information estimating apparatuses 100a and 100b include a spectrometer 110, a physiological information obtainer 120, and a processor 130.

The spectrometer 110 may obtain spectral absorbance data from a user. The spectrometer 110 may obtain the spectral absorbance data using various spectroscopic methods including infrared spectroscopy such as near-infrared (NIR), mid-infrared (MIR), and the like, or Raman spectroscopy. The spectral absorbance data may indicate a light absorption of a material, and the spectral absorbance may be represented in a frequency domain or a wavelength domain.

The spectrometer 110 may include: a light source 110a which emits light onto, an area of a user's skin; and a detector 110b which detects light reflected or scattered from the skin area. In this case, the user's skin area may be an upper portion of the wrist where veins or capillaries are located, or an area on the wrist that is adjacent to the radial artery. In a case in which the area is located on the path of the radial artery, measurement may be relatively less affected by external factors, such as the thickness of a skin tissue in the wrist, and may be robust against measurement errors. However, the skin area is not limited thereto, and may be peripheral portions of the body, such as lingers, toes, earlobes, and the like where blood vessels are densely located.

The light source 110a may be configured to emit light of various way length ranges to obtain spectral absorbance data more accurately. The light source 110a may be formed as an array of a plurality of light sources 110a to emit light of various wavelengths. For example, ire the case of using near-infrared spectroscopy, the light sources 110a may be configured to emit light in a near-infrared range (e.g., 1500 nm to 2500 nm). Further, in the case of using Raman spectroscopy, the light sources 110a may be configured to emit monochromatic laser light. The light source 110a may include a light emitting diode (LED), a laser diode (LD), a fluorescent body, and the like.

The detector 110b may include a photo diode, a photo transistor (PTr), an image sensor (e.g., CMOS image sensor), and the like. A plurality of detectors 110b may be provided, but the detector 110b is not limited thereto.

FIG. 2 is a graph illustrating optical wavelength versus absorbance of in vivo components, in which the absorbance is normalized based on the wavelength of 1400 nm. Examples of the in vivo components may include glucose, protein, fat, and water. As shown in the graph of absorbance normalized at 1400 nm, the absorbances of the in vivo components glucose, protein, fat, and water) are equal at 1400 nm, but are different at other wavelengths. For example, water has an absorbance peak at about 1450 nm while protein has a lower absorbance value than water at the same wavelength. As shown in the graph, the concentration or the amount of the in vivo components may be determined based on a difference in quantity of light detected at a plurality of wavelengths for various components such as glucose, protein, fat, water, and the like.

The physiological information obtainer 120 may obtain various types of metabolic and physiological information including the concentration of carbon dioxide ($CO_2$) discharged from a user. At least some functions of the physiological information obtainer 120 may be included in the processor 130.

For example, the physiological information obtainer 120 may include a gas sensor 120a for obtaining the concentration of $CO_2$. In this case, the gas sensor may include an optical gas sensor, a chemical gas sensor, and the like, but is not limited thereto. In an embodiment, the optical gas sensor 120a may be implemented as a $CO_2$ meter that determines a blood $CO_2$ concentration based on a difference between a first light and a second light that are reflected from the user and detected by a first photocell (e.g., a blue photocell) and a second photocell red photocell) of the physiological information obtainer 120, respectively.

The physiological information obtainer 120 may include a pulse wave sensor 120b for obtaining a pulse wave signal including a plethysmogram (PPG) signal. The pulse wave sensor ma include; one or more light sources 120c which emit light onto an object portion of a user; and a detector 120 which detects light scattered or reflected from the object portion. The light source 120c may include a light emitting diode (LED), a laser diode (ID), a fluorescent body, and the like. The detector 120d may include a photo diode, a photo, transistor (PTr), an image sensor (e.g., CMOS image sensor), and the like. In this case, the light source 120c and the detector 120d of die aforementioned spectrometer 110 may be shared.

Alternatively, the physiological information obtainer 120 may estimate the concentration of $CO_2$ based on the pulse wave signal obtained by the pulse wave sensor. In this case, the physiological information obtainer 120 may estimate the concentration of $CO_2$ based on the PPG signal by using various known methods.

The metabolic and physiological information may further include body temperature, heart rate (HR), heart rate variability (HRV), an initial estimated value of bio-information, a pulse wave feature, and the like, but is not limited thereto.

In addition, the physiological information obtainer 120 may further include a body temperature sensor 120e for measuring a body temperature. Further, the physiological information obtainer 120 may estimate the body temperature from a user's skin by using absorbance obtained by the spectrometer 110. In this case, the physiological information obtainer 120 may estimate the body temperature based on a pre-defined linear/non-linear correlation between the absorbance and body temperature of skin. In another example, the body temperature sensor 120e may be an infrared thermometer or a laser thermometer that infers a temperature of an object from black-body radiation emitted by the object.

The physiological information obtainer 120 may further include a electrocardiogram sensor 120f for obtaining the heart rate and/or the heart rate variability. Alternatively, the physiological information obtainer 120 may obtain the heart rate and/or the heart rate, variability based on the pulse wave signal obtained by the pulse wave sensor 120b.

The physiological it obtainer 120 may obtain an initial estimated value of bio-information based on the absorbance obtained by the spectrometer 110. For example, the physiological information obtainer 120 may obtain the initial estimated value of bio-information using Lambert-Beer's law, Partial Least Squares, and the like. For example, the following Equations 1 and 2 represent equations for estimating blood glucose among bio-information, and the physiological information obtainer 120 may obtain the initial estimated blood glucose value by using the equation for estimating blood glucose. However, the equation for estimating blood glucose is not limited to Equations 1 and 2 defined herein.

$$FS = BS + \varepsilon_g \cdot L \cdot \Delta C_t \quad \text{[Equation 1]}$$

Herein, BS denotes a background spectrum measured at a reference time (e.g., a time when a subject is on an empty stomach), in which the background spectrum may include a blood glucose component that is measured at a time when the subject is on an empty stomach, and may also include noise: $\varepsilon_g$ denotes a unit blood glucose spectrum; and L denotes a light travel path. In this case, the unit blood glucose spectrum and the light travel path are previously input values. $\Delta C_t$ denotes a variation in blood glucose concentration. $\varepsilon_g \cdot L \cdot \Delta C_t$ denotes a blood glucose component signal.

The following Equation 2 represents an equation for obtaining the initial estimated value of blood glucose.

$$C_t = \Delta C_t + C_0 \quad \text{[Equation 2]}$$

Herein, $C_0$ denotes a reference blood glucose value, which is a blood glucose value at a calibration time (e.g a time when a subject is cm an empty stomach), and $C_t$ denotes an initial estimated blood glucose value. It is generally assumed that the blood glucose value $C_0$ on an empty stomach is constant, such that upon obtaining the blood glucose variation $\Delta C_t$ using Equation 1, the initial estimated blood glucose value $C_t$ may be obtained using Equation 2.

The physiological information obtainer 120 may obtain a feature (e.g., blood glucose), which has a high correlation with bio-information to be obtained, using the pulse wave signal. For example, the feature, obtained by analyzing a waveform of the pulse wave signal, may include a time and/or an amplitude of a maximum point of the pulse wave signal, a time and/or an amplitude of a minimum point of the pulse wave signal, a time difference between two points of the pulse wave signal, and the like, but is not limited thereto.

Each sensor of the physiological information obtainer 120 may be mounted in the bio-information estimating apparatuses 100a and 100b, or may be separately manufactured as an external hardware device.

The physiological information obtainer 120 may display information to guide a user to enter metabolic and physiological information, and may obtain the metabolic and physiological information by an input of the user.

The processor 130 may estimate lino information based on the obtained absorbance and/or the obtained metabolic and physiological information by using a predictive model corresponding to the obtained absorbance and/or the obtained metabolic and physiological information.

For example, the processor 130 may collect a plurality of absorbance data and/or a plurality of metabolic and physiological information items as training data, and may pre-generate a predictive model by using the collected training data. In this case, the processor 130 may obtain a plurality of types of training data by combining the absorbance with different types of metabolic and physiological information, and may generate a predictive model for each type of the training data by using the types of the training data. For example, the following Table 1 shows some types of the training data which may be defined, but the training data is not, limited thereto.

| Type | Training data |
| --- | --- |
| Type 1 | Combination of absorbance and concentration of carbon dioxide |
| Type 2 | Combination of absorbance, concentration of carbon dioxide, and body temperature |
| Type 3 | Combination of absorbance, concentration of carbon dioxide, and heart rate |
| Type 4 | Combination of absorbance, concentration of carbon dioxide, and heart rate variability |
| Type 5 | Combination of absorbance, concentration of carbon dioxide, body temperature, and heart rate |
| Type 6 | Combination of absorbance, concentration of carbon dioxide, body temperature, heart rate, and heart rate variability |
| Type 7 | Combination of initial estimated value of bio-information, concentration of carbon dioxide, body temperature, and heart rate |
| Type 8 | Combination of initial estimated value of bio-information, concentration of carbon dioxide, and pulse wave feature |

For example, the processor 130 may generate the predictive model by using a Recursive Neural Network (RNN). However, the predictive model is not limited thereto, and may be generated using linear regression analysis, non-linear regression analysis, Partial Least Squares (PIS), Bayesian Network, Hidden Markov Model, Decision Tree, Random Forest, Support Vector Machine, Convolutional Neural Network, Deep Neural Network, and the like.

Figure 3A:
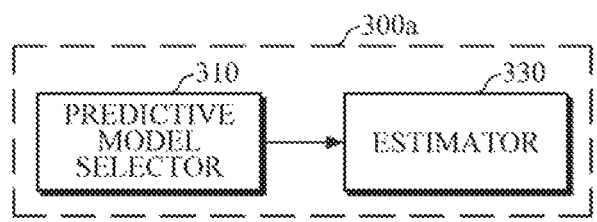
FIGS. 3A and 3B are block diagrams illustrating a configuration of a processor according to embodiments of the present disclosure.
Figure 3B:
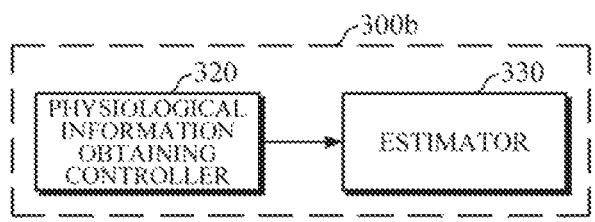

FIGS. 3A and 3B are block diagrams illustrating a configuration of a processor according to embodiments of the present disclosure. Various embodiments of estimating bio-information will be described below with reference to FIGS. 3A and 3B.

Referring to FIG. 3A, a processor 300a according to an embodiment of the present disclosure includes a predictive model selector 310 and an estimator 330.

The predictive model selector 310 may select a predictive model for use in estimating bio-information from among a plurality of predictive models based on absorbance and/or types of metabolic and physiological information. In particular, the plurality of predictive models may be generated for each of the types of training data obtained by combining the absorbance with the various types of metabolic and physiological information in a plurality of different manners, as described above.

For example, types of sensors mounted in the bio-information estimating apparatuses 100a and 100b are different for each of the bio-information estimating apparatuses 100a and 100b, such that different metabolic and physiological information may be obtained by each of the bio-information estimating apparatuses 100a and 100b of users. Alternatively, the metabolic and physiological information to be obtained may vary depending on computing performance of the bio-information estimating apparatuses 100a and 100b, user characteristics, a sensor operating state at a measurement time, and the like.

Accordingly, the predictive model selector 310 may confirm a type of the metabolic and physiological information obtained by the physiological information obtainer 120, and may select a predictive model corresponding to absorbance and/or a type of metabolic and physiological information. For example, in the case where the obtained information is the absorbance and the concentration of carbon dioxide, the predictive model selector 310 may select a predictive model of type 1 described above.

Further, the predictive model selector 310 may check an operating state of the spectrometer 110 and each sensor, user characteristics (e.g., age, sex, health condition, etc.), computing performance, and the like, and may select a predictive model based on the checking result. For example, in a case in which a specific sensor does not operate at a current measurement time and thus no metabolic and physiological information is not obtained by the sensor, in a case in which accuracy of the metabolic and physiological information of the specific sensor is not high, or in a case in which it is determined that accuracy of specific metabolic and physiological information obtained in view of user characteristics is not high, the predictive model selector 310 may select a predictive model based on other information items except the metabolic and physiological information.

The estimator 330 may input information items, which corresponds to the selected predictive model and are selected from among the obtained absorbance and metabolic and physiological information, into the predictive model, and may obtain an output of the predictive model as an estimated bio-information value.

Figure 4:
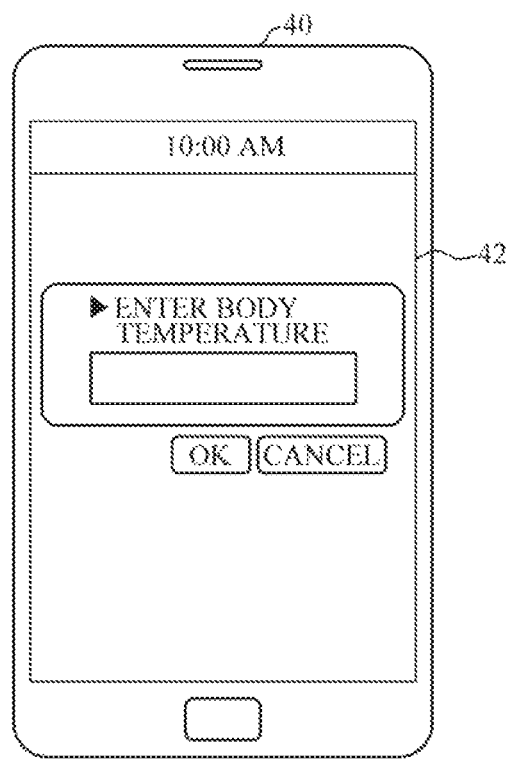
FIG. 4 is a diagram illustrating an example of obtaining metabolic and physiological information.

Referring to FIG. 3B, a processor 300b according to an embodiment of the present disclosure includes a physiological information obtaining controller 320 and an estimator 330. FIG. 4 is a diagram illustrating, an example of obtaining metabolic and physiological information.

The physiological information obtaining controller 320 may control obtaining metabolic and physiological information based on the predictive model for use in estimating bio-information. For example, upon receiving a request for estimating bio-information, the physiological information obtaining controller 320 checks an operating state of the spectrometer 110 and each sensor (e.g., the gas sensor 120a, the pulse wave sensor 120b including the light source 120c and the detector 120d, the body temperature sensor 120e, and the electrocardiogram sensor 120f) of the physiological information obtainer 120, and may control operation of the spectrometer 110 and each sensor or may provide guidance on the operation for a user.

For example, when a default predictive model for use in estimating bio-information is a predictive model of type 2 described above, the physiological information obtaining controller 320 may check an operating state of the mounted spectrometer 110, body temperature sensor 120e, and the like; and if the operating state is an OFF state, the physiological information obtaining controller 320 may, directly switch the operating state to an ON state, or may output a guidance message or a voice message for requesting a user to operate the sensors. Alternatively, in a case in which no body temperature sensor is embedded or a failure occurs in the body temperature sensor 120e, the physiological information obtaining controller 320 may control the physiological information obtainer 120 to obtain body temperature information based on the absorbance.

In addition, as illustrated in FIG. 4, in a case in which a failure occurs in the embedded body temperature sensor 120e, the bio-information estimating apparatuses 100a and 100b may provide an interface on a display 42 of a smartphone 40 which includes the bio-information estimating apparatuses 100a and 100b, so as to enable a user to directly enter body temperature information measured using an external thermometer and the like. However, the metabolic and physiological information is not limited thereto, and the physiological information obtaining controller 320 may enable a user to enter desired metabolic and physiological information by voice, in which the user may enter the information by using a voice input device such as a microphone and the like.

The estimator 330 may input the absorbance and/or the metabolic and physiological information, which are obtained based on the predictive model, into the predictive model, and may obtain an output of the predictive model as an estimated bio-information value.

Referring to FIG. 1B, the bio-information estimating apparatus 100b according to the embodiment of the present disclosure may further include an output interface 140, a storage 150, and a communication interface 160.

The output interface 140 may output results processed by the spectrometer 110, the physiological information obtainer 120, and the processor 130. For example, the output interface 140 may visually output the estimated bio-information value through a display module. Alternatively, the output interface 140 may output the value in a non-visual manner by voice, vibrations, tactile sensation, and the like using a speaker module, a haptic module, and the like. In this case, if the estimated bio-information value falls outside a preset normal range, the output interface 140 may also output warning information in various manners, such as highlighting an abnormal value in red and the like, displaying the abnormal value along with a preset normal range, outputting a voice warning message, adjusting a vibration intensity, and the like.

The storage 150 may store results processed by the spectrometer 110, the physiological information obtainer 120, and the processor 130. Further, the storage 150 may store various types of reference information required for estimating bio-information. For example, the reference information may include user characteristic information such as a user's age, sex, health condition, and the like. In addition, the reference information may include information such as one or more predictive models and the like, but is not limited thereto.

In this case, the storage 150 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 160 may communicate with an external device 170 using various wired or wireless communication techniques, and may transmit and receive various data to and from the external device 170. For example, the communication interface 160 may transmit an estimation result of bio-information to the external device 170, and may receive various types of information, such as a predictive model required for estimating bio-information, from the external device 170. In this case, the external device 170 may include an information processing device such as a smartphone, a tablet PC, a desktop computer, a laptop computer, and the like.

The communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, third generation (3G) communication, fourth generation (4G) communication, fifth generation (5G) communication, and the like, but are not limited thereto.

Figure 5:
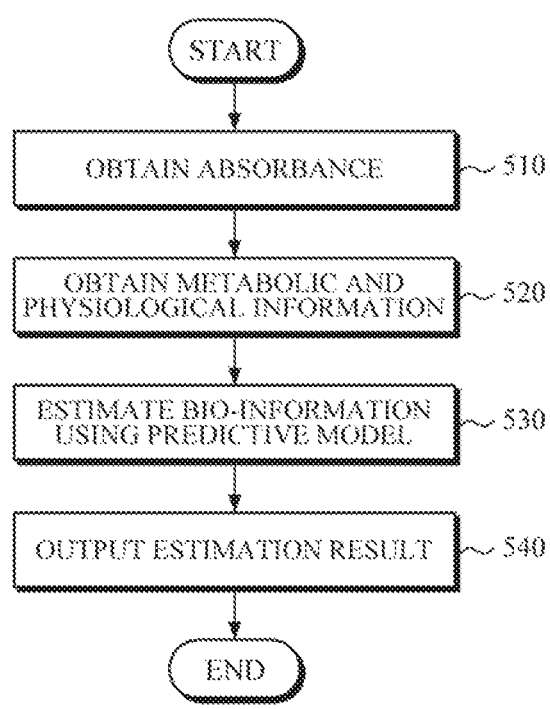
FIG. 5 is a flowchart illustrating a method of estimating bio-information according to an embodiment of the present disclosure.

FIG. 5 is a flowchart illustrating a method of estimating bio-information according to an embodiment of the present disclosure. The bio-information estimating method of FIG. 5 may be an example of a bio-information estimating method, performed by the bio-information estimating apparatuses 100a and 100b.

Upon receiving a request for estimating bio-information, the bio-information estimating apparatuses 100a and 100b may obtain absorbance data from a user by using a spectrometer 110 in operation 510. In this case, the request for estimating bio-information may be input by a user, or may be generated automatically at predetermined intervals for continuous measurements. Alternatively, the request may be received from an external device 170.

Further, the bio-information estimating apparatuses 100a and 100b may obtain metabolic and physiological information including the concentration of carbon dioxide in operation 520. In this case, in addition to the concentration of carbon dioxide, the metabolic and physiological information may further include body temperature, heart rate (HR), heart rate variability (HRV), an initial estimated value of bio-information, a pulse wave feature, and the like. The bio-information estimating apparatuses 100a and 100b may obtain the metabolic and physiological information simultaneously with or separately from the operation 510 by using various sensors mounted in the bio-information estimating apparatuses 100a and 100b. Alternatively, the bio-information estimating apparatuses 100a and 100b may obtain body temperature information and the like by using the absorbance data obtained in operation 510.

In a case in which there is a default predictive model for use in estimating bio-information in operation 520, the bio-information estimating apparatuses 100a and 100b may obtain metabolic and physiological information required for the default predictive model. For example, in a case in which the default predictive a model requires body temperature information, the bio-information estimating apparatuses 100a and 100b may check whether a body temperature sensor 120e operates; and in a case in which the body temperature sensor 120e does not operate, the bio-information estimating apparatuses 100a and 100b may directly control operation of the body temperature sensor 120e, may provide information on an operating state of the body temperature sensor 120e, or may obtain body temperature information based on other information (e.g., absorbance) or through a user input. On the other hand, in a case in which the default predictive model does not require body temperature information, the bio-information estimating apparatuses 100a and 100b may switch the body temperature sensor 120e to an OFF state for improving computing performance, rapid processing, and the like.

Then, upon obtaining the absorbance and the metabolic and physiological information, the bio-information estimating apparatuses 100a and 100b may estimate bio-information by using the predictive model in 530.

In addition, a plurality of types of predictive models may be generated based on the types of metabolic and physiological information; and upon obtaining the metabolic and physiological information from a user in operation 520, the bio-information estimating apparatuses 100a and 100b may select an appropriate type of the predictive model from among the plurality of predictive models based on a type of the obtained metabolic and, physiological information, based on a mapping table in which each type of the predictive model is mapped to each type of the obtained metabolic and physiological information.

Subsequently, the bio-information estimating apparatuses 100a and 100b may output an estimation result of bio-information in 540. For example, the bio-information estimating apparatuses 100a and 100b may visually output the estimation result through a display, or may output the estimation result in a non-visual manner by voice, vibrations, tactile sensation, and the like using a speaker module and/or a haptic module.

Figure 6:
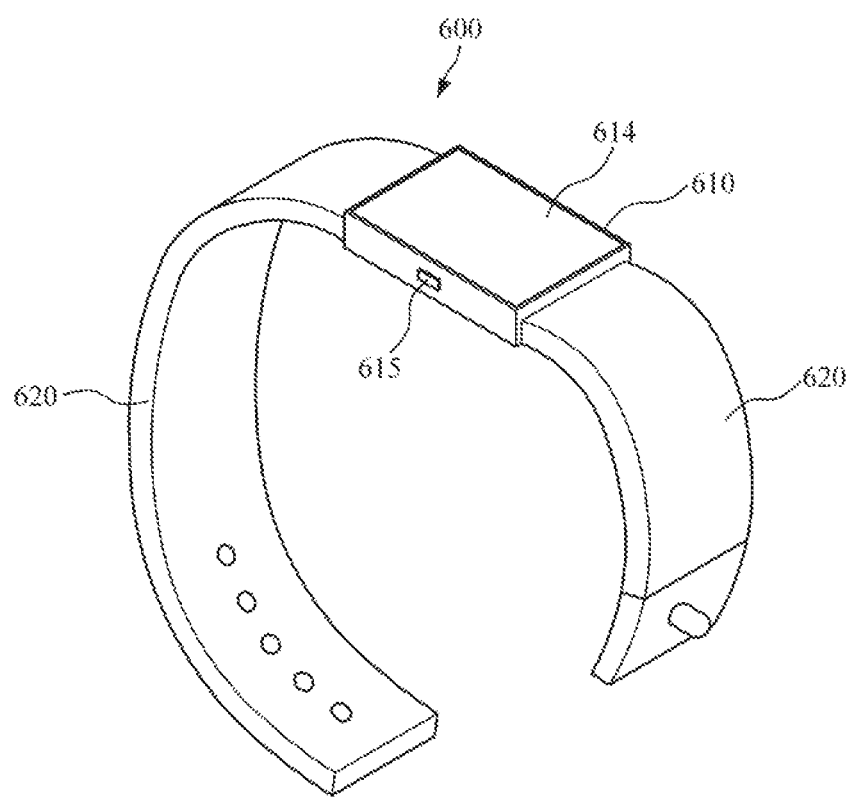
FIG. 6 is a diagram illustrating, an example of a wearable device according to an embodiment of the present disclosure.

FIG. 6 is a diagram illustrating an example of a wearable device according to an embodiment of the present disclosure.

As illustrated in FIG. 6, various embodiments of the bio-information estimating apparatuses 100a and 100b may be mounted in a smart band-type or a smart watch-type wearable device. However, this is merely an example for convenience of explanation, and the bio-information estimating apparatuses 100a and 100b are not limited thereto and may be mounted in various information processing devices such as a smartphone, a tablet PC, a desktop computer, and the like.

Referring to FIG. 6, the wearable device 600 includes a main body 610 and a strap 620.

The strap 620 may be flexible, and may be bent to be wrapped around a user's wrist or may be bent in a manner which allows the strap 620 to be detached from the wrist. In this case, a battery may be embedded in the main body 610 or the strap 620 to supply power to various modules of the wearable device 600.

A spectrometer 110, which obtains spectral absorbance data by emitting light onto a user's skin and detecting light scattered or reflected from the skin, may be disposed in an inner space of the main body 610 of the wearable device 600. In particular, the spectrometer 110 may obtain the absorbance data using near-infrared spectroscopy, Raman spectroscopy, and the like.

Further, the spectrometer 110 may include a Linear Variable Filter (LVF), The LVF has spectral properties which vary linearly over the entire length. Accordingly, the LVF may scatter the incident light in order of wavelengths. Although having a compact size, the LVF has excellent light scattering ability.

In addition, the main body 610 of the wearable device 600 may include a gas sensor 120a, a pulse wave sensor 120b, an electrocardiogram sensor 120f and/or a body temperature sensor 120e for obtaining various types of metabolic and physiological information such as the concentration of carbon dioxide, body temperature, heart rate, heart rate variability, and the like.

Moreover, the maim body 610 of the wearable device 600 may include a processor 130 which estimates biological components of a user by inputting the spectral absorbance data, obtained by the spectrometer 110, and metabolic and physiological information, obtained by various other sensors, into a predictive model. The processor 130 may obtain additional metabolic and physiological information by using the absorbance data and the metabolic and physiological information obtained using other sensors. For example, the processor 130 may obtain the concentration of carbon dioxide and/or pulse wave features, heart rate, and the like based on the pulse wave signal obtained by the pulse wave sensor 120b.

In this case, the processor 130 may control the sensors or may obtain required metabolic and physiological information based on a type of information to be input into a default predictive model.

In addition, the processor may select a predictive model for use in estimating bio-information from among a plurality of predictive models based on the obtained absorbance and the type of the metabolic and physiological information. In this case, the plurality of predictive models may be generated by variously combining the absorbance with the metabolic and physiological information, and may be stored in a storage 150.

A display 614, which provides various types of information for a user, may be disposed at a front surface of the main body 610 of the wearable device 600. The display 614 may be formed as a touch panel which allows a user to perform touch input, and may receive the user's touch input and transmit the touch input to the processor. The display 614 may visually output a processing result of the processor under the control of the processor.

Further, the main body 610 of the wearable device 600 may include a manipulator 615 which allows a user to enter a command for controlling various functions of the wearable device 600. The manipulator 615 may be electrically connected to the processor, and may transmit, various control commands of the user to the processor. Further, the manipulator 615 may include a power button for inputting a command to turn on/off the wearable device 600.

The processor may store various processing results in a storage device. The storage device may be mounted in the main body 610 of the wearable device 600, or may be mounted in an external device which may be connected by wire or wirelessly to the wearable device 600 through a communication nodule if the wearable device 600.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
   a spectrometer configured to obtain a light absorbance spectrum and a plethysmogram (PPG) signal from a user;
   one or more sensors configured to obtain metabolic and physiological information of the user, the obtained metabolic and physiological information including a carbon dioxide ($CO_2$) concentration of the user; and
   a processor configured to identify a predictive model corresponding to a type of the obtained metabolic and physiological information, among a plurality of predictive models trained based on different combinations of a reference light absorbance spectrum and a plurality of metabolic and physiological information types, and estimate blood glucose of the user based on the PPG signal, the $CO_2$ concentration, and the metabolic and physiological information by using the identified predictive model.

2. The apparatus of claim 1, wherein the spectrometer comprises:
   a light source configured to emit a light onto the user; and
   a detector configured to detect the light scattered or reflected from the user,
   wherein the spectrometer is further configured to obtain the PPG signal based on the detected light.

3. The apparatus of claim 1, wherein the one or more sensors comprise an optical gas sensor configured to obtain the $CO_2$ concentration of the user.

4. The apparatus of claim 1, wherein the metabolic and physiological information further comprises a body temperature and a heart rate of the user.

5. The apparatus of claim 1, wherein the one or more sensors comprise:
   a body temperature sensor configured to measure a body temperature of the user; and
   an electrocardiogram sensor configured to obtain a heart rate of the user.

6. The apparatus of claim 4, wherein the one or more sensors are further configured to estimate the body temperature based on the obtained light absorbance spectrum.

7. The apparatus of claim 4, wherein the one or more sensors comprise a pulse wave sensor configured to obtain the PPG signal,
   wherein the processor is further configured to obtain the heart rate based on the PPG signal.

8. The apparatus of claim 1, wherein upon receiving a request for estimating the bio-information, the processor checks an operating state of the spectrometer and each of the one or more sensors, and selects the predictive model for use in estimating the blood glucose from among the plurality of predictive models based on a result of checking the operating state.

9. The apparatus of claim 1, wherein upon receiving a request for estimating the bio-information, the processor checks an operating state of the spectrometer and each of the one or more sensors, and controls an operation of the spectrometer or the each of the one or more sensors or provides guidance on the operation for the user based on the predictive model for use in estimating the bio-information.

10. The apparatus of claim 1, wherein the predictive model is generated by using one of linear regression analysis, non-linear regression analysis, Partial Least Squares (PLS), Bayesian Network, Hidden Markov Model, Decision Tree, Random Forest, Support Vector Machine, Convolutional Neural Network, and Deep Neural Network.

11. The apparatus of claim 1, further comprising an output interface configured to output at least one of the obtained light absorbance spectrum, the obtained metabolic and physiological information, and a processing result of the processor.

12. A method of estimating bio-information, the method comprising:
   obtaining a light absorbance spectrum and a plethysmogram (PPG) signal from a user;
   obtaining metabolic and physiological information of the user, the metabolic and physiological information including a concentration of carbon dioxide ($CO_2$) of the user;
   identifying a predictive model corresponding to a type of the obtained metabolic and physiological information, among a plurality of predictive models trained based on different combinations of a reference light absorbance spectrum and a plurality of metabolic and physiological information types, and
   estimating blood glucose of the user based on the obtained PPG signal, the $CO_2$ concentration, and the obtained metabolic and physiological information by using the identified predictive model.

13. The method of claim 12, wherein the metabolic and physiological information further comprises a body temperature and a heart rate,
   wherein the estimating the blood glucose comprises estimating the blood glucose based on the PPG signal, the $CO_2$, the body temperature, and the heart rate of the user, by using the identified predictive model.

14. The method of claim 12, wherein the obtaining the light absorbance spectrum is performed by a spectrometer, and the obtaining metabolic and physiological information is performed by one or more sensors, and
   wherein the estimating the bio-information comprises, upon receiving a request for estimating the bio-information, checking an operating state of the spectrometer and each of the one or more sensors, and selecting the predictive model based on a result of checking the operating state of the spectrometer and each of the one or more sensors.

15. The method of claim 12, wherein the obtaining the light absorbance spectrum is performed by a spectrometer, and the obtaining metabolic and physiological information is performed by one or more sensors, and wherein the estimating the bio-information comprises, upon receiving a request for estimating the bio-information, checking an operating state of the spectrometer and each of the one or more sensors, and controlling an operation of the spectrometer or each of the one or more sensors, and providing the user with guidance on the operation based on the identified predictive model.

16. The method of claim 12, further comprising outputting at least one of the obtained light absorbance spectrum, the obtained metabolic and physiological information, and the estimated blood glucose.

17. The method of claim 12, wherein the different combinations of the reference light absorbance spectrum with the plurality of metabolic and physiological information types comprise a combination of the reference light absorbance spectrum and a reference carbon dioxide concentration.

18. The method of claim 12, wherein the different combinations of the reference light absorbance spectrum with the plurality of metabolic and physiological information types comprise:

a first combination of the reference light absorbance spectrum and a reference carbon dioxide concentration;

a second combination of the reference light absorbance spectrum, the reference carbon dioxide concentration, and a reference body temperature;

a third combination of the reference light absorbance spectrum, the reference carbon dioxide concentration, the reference body temperature, and a reference heart rate;

a fourth combination of the reference light absorbance spectrum, the reference carbon dioxide concentration, the reference body temperature, the reference heart rate, and a reference heart rate variability; and a fifth combination of the reference light absorbance spectrum, the reference carbon dioxide concentration, the reference body temperature, the reference heart rate, the reference heart rate variability, and a reference pulse wave feature.

19. The method of claim 18, wherein the identifying the predictive model comprises identifying the predictive model which is trained based on one of the first to the fifth combinations, as the predictive model for estimating the bio-information.

\* \* \* \* \*